United States Patent
Wang

(10) Patent No.: US 12,057,221 B2
(45) Date of Patent: Aug. 6, 2024

(54) PROGRAM CONTROL SYSTEM AND METHOD FOR IMPLANTABLE ELECTRONIC DEVICE

(71) Applicant: MICROPORT SOARING CRM (SHANGHAI) CO., LTD., Shanghai (CN)

(72) Inventor: Li Wang, Shanghai (CN)

(73) Assignee: MICROPORT SOARING CRM (SHANGHAI) CO., LTD., Shanghai (CN)

( * ) Notice: Subject to any disclaimer, the term of this patent is extended or adjusted under 35 U.S.C. 154(b) by 986 days.

(21) Appl. No.: 16/980,329

(22) PCT Filed: Mar. 12, 2019

(86) PCT No.: PCT/CN2019/077774
§ 371 (c)(1),
(2) Date: Sep. 11, 2020

(87) PCT Pub. No.: WO2019/174565
PCT Pub. Date: Sep. 19, 2019

(65) Prior Publication Data
US 2021/0043315 A1 Feb. 11, 2021

(30) Foreign Application Priority Data
Mar. 12, 2018 (CN) .......................... 201810200400.5

(51) Int. Cl.
*G16H 40/40* (2018.01)
*G16H 40/67* (2018.01)
*G16H 50/20* (2018.01)

(52) U.S. Cl.
CPC ............. *G16H 40/40* (2018.01); *G16H 40/67* (2018.01); *G16H 50/20* (2018.01)

(58) Field of Classification Search
CPC .......... G06F 8/65; G06F 21/606; G06F 21/30; G06F 21/44; G06F 2221/2103;
(Continued)

(56) References Cited

U.S. PATENT DOCUMENTS

2009/0058635 A1 3/2009 LaLonde et al.
2010/0152815 A1 6/2010 Vandanacker
(Continued)

FOREIGN PATENT DOCUMENTS

CN 101354751 A 1/2009
CN 201921316 U 8/2011
(Continued)

*Primary Examiner* — Dionne Pendleton
(74) *Attorney, Agent, or Firm* — Muncy, Geissler, Olds & Lowe, P.C.

(57) ABSTRACT

The present invention relates to the field of medical devices and discloses a program control system and method for an implantable electronic device. The program control system includes at least one communication device, at least one terminal device and a cloud server communicatively connected to both the communication device and the terminal device. The communication device is configured to acquire feedback data from the implantable electronic device (IED) and upload the feedback data to the cloud server. The cloud server is configured to process the feedback data and store the processed feedback data. The terminal device is configured to retrieve the processed feedback data from the cloud server for enquiry by a user. In the present invention, there is also provided a program control method for an implantable electronic device. The present invention entails a processing mode for use on a cloud platform in which individual components in the program control system can be separately upgraded in a timely manner, thus lowering the hardware upgrading cost and achieving more scientific analysis and management of data.

8 Claims, 5 Drawing Sheets

(58) Field of Classification Search
CPC .... G06F 8/656; G06F 21/552; G06F 21/6272; G06F 2221/2109; G06F 2221/2111; G06F 2221/2151; G06F 21/82; G06F 2221/2101; G06F 2221/2107; G06F 2221/2115; G06F 8/60; G16H 40/40; G16H 40/67; G16H 50/20; G16H 10/65; G16H 20/30; G16H 30/20; G16H 40/20; G16H 40/63; G16H 10/60; G16H 50/30; H04L 67/12; H04L 69/08; H04L 63/0478; H04L 67/06; H04L 67/10; H04L 67/1097; H04L 2209/80; H04L 63/0442; H04L 67/51; H04L 9/08; H04L 9/30; H04L 63/0428; H04L 63/18; H04L 67/025; Y04S 40/18; Y04S 40/20; Y04S 40/00; A61F 2250/0002; B81B 2201/02; B81B 2201/06; G06K 7/10386; G06K 7/10425; G06K 19/0723; G06K 7/10009; G06K 7/10217; H04Q 2209/00; H04Q 2209/47; H04Q 2209/50; H04Q 2209/86; H04Q 9/00; H04Q 2209/43; H04Q 2209/886; A61N 1/36128; A61N 1/37235; A61N 1/37247; A61N 1/37282; A61N 1/37217; A61N 1/37254; A61N 1/37211; A61N 1/37264; A61N 1/36135; A61N 1/3702; A61N 1/3937; A61N 1/37252; A61B 5/0031; A61B 5/0215; A61B 5/318; A61B 90/98; A61B 5/4842; A61B 5/686; A61B 5/0024; A61B 5/01; A61B 5/02438; A61B 5/14503; A61B 5/14532; A61B 5/1473; A61B 5/6847; A61M 31/00; G16Z 99/00; H04W 12/02; H04W 4/80; H04W 12/04; H04W 12/06; H04W 4/90; H04W 84/20; H04W 88/04; H04W 12/033; H04W 12/0431; H04W 4/02; H04W 4/029; H04W 4/20; H04W 88/02; H04W 12/08; H04W 12/126; H04W 12/61; H04W 12/63; H04W 12/00

See application file for complete search history.

(56) References Cited

U.S. PATENT DOCUMENTS

| | | | |
|---|---|---|---|
| 2013/0204327 A1* | 8/2013 | Carlton | G16H 40/63 607/59 |
| 2018/0043172 A1* | 2/2018 | Serrano Carmona | A61N 1/36132 |
| 2018/0247095 A1* | 8/2018 | Sundaram | G06K 7/10425 |

FOREIGN PATENT DOCUMENTS

| | | |
|---|---|---|
| CN | 103051731 A | 4/2013 |
| CN | 103562967 A | 2/2014 |
| CN | 104225790 A | 12/2014 |
| CN | 104548230 A | 4/2015 |
| CN | 104683474 A | 6/2015 |
| CN | 204442424 U | 7/2015 |
| CN | 204909435 U | 12/2015 |
| CN | 105212920 A | 1/2016 |
| CN | 105930668 A | 9/2016 |
| CN | 106073798 A | 11/2016 |
| CN | 106356924 A | 1/2017 |
| CN | 106861044 A | 6/2017 |
| EP | 3091459 A1 | 11/2016 |

* cited by examiner

PROGRAM CONTROL SYSTEM AND METHOD FOR IMPLANTABLE ELECTRONIC DEVICE

TECHNICAL FIELD

The present invention relates to the field of medical devices and, in particular, to program control systems and method for an implantable electronic device.

BACKGROUND

Existing implantable electronic devices (IEDs) include insulin infusion pumps, brain pacemakers, cardiac pacemakers and other medical devices that can be implanted in patients' bodies. For example, as IEDs, cardiac pacemakers are used as a main treatment approach for arrhythmia patients. During the implantation of such an IED and post-implantation follow-up, it is necessary to read and configure parameters of the cardiac pacemaker using a supporting programmer in order to assess the operating condition of the cardiac pacemaker and treatment response in the patient. Therefore, the programmer is important to the cardiac pacemaker system.

An IED system consists essentially of two components: the implantable electronic device and a supporting programmer. The implantable electronic device is configured to be implanted in the body of a patient and then communicate and interact with the supporting programmer in a wireless manner. The programmer is configured for receipt and analysis of various data from the IED, analysis and storage of various parameters, and issuance of programmed control commands. A medical care practitioner can assess treatment response in the patient by analyzing the IED's parameters using the programmer.

The inventors have found that there are at least the following problems in the prior art: the existing programmers are fabricated as medical-grade computers (laptop or desktop) with dedicated software running thereon, they are expensive in price and their sales are extremely low, when compared to general-purpose computers. For these reasons, most of the programmers are required to guarantee a long service life in order to amortize the high cost over a long term. The current rapid development of medical and computer technologies necessitates upgrading of programmers in software, hardware and other aspects. However, in terms of hardware, the conventional programmers only allow expensive overall upgrading, but not upgrading of individual components. In addition, software upgrading of such programmers often requires the manufacturers to dispatch their technicians to the hospitals using their products. This is very inflexible and costly in human resources. Therefore, the existing programmers are generally used just as delivered from factory and seldom upgraded in software or hardware.

Furthermore, for safety considerations, the existing programmers are stand-alone operation, unable to communicate via the network and locally controlled by their IED systems, with the results of parameter analysis and so on being displayed only on the local programmers. This requires in-field presence of physicians or manufacturers' technicians.

SUMMARY OF THE INVENTION

It is an objective of the present invention to provide program control systems and method for an implantable electronic device, which entail a processing mode for use on a cloud platform, in which individual components in the program control systems can be separately upgraded in a timely manner, thus lowering the hardware upgrading cost and achieving more scientific data analysis and management. In addition, operational convenience may be provided to a patient, a physician and a technician of the manufacturer who may be in different locations.

The above objective is attained by a program control system for an implantable electronic device provided in embodiments of the present invention, which includes at least one communication device, at least one terminal device and a cloud server communicatively connected to both the communication device and the terminal device, the communication device configured to acquire feedback data from the implantable electronic device and upload the feedback data to the cloud server, the cloud server configured to process the feedback data and store the processed feedback data the terminal device configured to retrieve the processed feedback data from the cloud server for enquiry by a user.

In embodiments of the present invention, there is also provided a program control method for an implantable electronic device, for use on a cloud server. The program control method includes: receiving, via a network, feedback data from at least one implantable electronic device uploaded by a communication device; processing the feedback data and storing the processed feedback data, wherein the processed feedback data is available for retrieval by a user.

In embodiments of the present invention, there is also provided a program control system for an implantable electronic device, which includes at least one communication device and a server communicatively connected to the communication device, the communication device configured to acquire feedback data from the implantable electronic device and upload the acquired feedback data to the server, the server configured to process the feedback data and store the processed feedback data, wherein the processed feedback data is available for retrieval by a user from the server.

In embodiments of the present invention, there is also provided a program control system for an implantable electronic device, which includes at least one communication device and a cloud server communicatively connected to the communication device, the communication device configured to acquire feedback data from the implantable electronic device and upload the acquired feedback data to the server, the cloud server configured to process the feedback data and store the processed feedback data, wherein the processed feedback data is available for retrieval by a user from the cloud server via a terminal device.

Compared to the conventional programmers, embodiments of the present invention entail a program control system distributed in terms of functions and components. That is, the program control system is composed of physically separate components including the communication device and the cloud server. In this way, the various components in the program control system can be hardware upgraded separately. That is, hardware of each of the communication device, the terminal device and the cloud server can be independently upgraded. Therefore, the program control system of this application is reduced in hardware upgrading cost (compared to the existing programmers, which must be overall replaced for hardware upgrading). Moreover, software upgrading of each component in the program control system is allowed to be achieved in a timely and individual way (any component can be immediately upgraded upon a new software version becoming available)

so that the latest advancements in the medical science and technology can be applied to the various components in the program control system to result in more scientific feedback data analysis and management. These make upgrading an easy task. Further, the program control system entails a processing mode for use on a cloud platform, in which the communication device acquires feedback data from the IED deployed in the patient's body and uploads the acquired feedback data to the cloud server for processing. The manufacturer's technician and the physician can retrieve the processed feedback data from the cloud server onto their terminal devices and know conditions of the patient from the data. This provides operational convenience to the patient, the physician and the technician who may be in different locations. Furthermore, storing the processed feedback data on the cloud server can prevent loss of such data and enable consistent analysis over a long history.

Additionally, in the program control system, the communication device may includes a first transmission module, a second transmission module and a data conversion module connected to both the first and second transmission modules, the first transmission module configured to acquire feedback data in a first format from the implantable electronic device, the data conversion module configured to convert the feedback data from the first format into a second format, the second transmission module configured to upload the feedback data in the second format to the cloud server.

Additionally, in the program control system, the first transmission module may include at least one of a short-range wireless communication module, a long-range RF identification module and a network cable interface, and the second transmission module may include at least one of a wireless network module and a network cable interface.

Additionally, in the program control system, the terminal device may include a third transmission module, a control module, an input module and a display module, the control module connected to all of the third transmission module, the input module and the display module, the control module configured to acquire the processed feedback data from the cloud server via the third transmission module and cause the display module to display the processed feedback data, the input module configured to input adjustment commands for the implantable electronic device, the control module further configured to transmit the adjustment commands to the cloud server via the third transmission module, the cloud server further configured to receive the adjustment commands, generate adjustment data for the implantable electronic device, and transmit the adjustment data to the implantable electronic device via the communication device, thereby effecting corresponding adjustments in the implantable electronic device.

Additionally, in the program control system, the cloud server may be further configured to receive post-adjustment feedback data from the implantable electronic device via the communication device and transmit the post-adjustment feedback data to the terminal device for enquiry by the user.

Additionally, in the program control system, the cloud server may include a cloud processor and a cloud storage device, the cloud processor configured to process the feedback data and store the processed feedback data on the cloud storage device.

Additionally, the program control method may further include, upon receipt of an enquiry request from a terminal device of the user via the network, transmitting the processed feedback data to the terminal device for enquiry by the user.

Additionally, the program control method may further include: determining whether adjustment commands for the implantable electronic device have been received from the terminal device of the user via the network; if such adjustment commands have been received, generating adjustment data for the implantable electronic device based on the adjustment commands; and transmitting the adjustment data to the implantable electronic device via the communication device, thereby effecting corresponding adjustments in the implantable electronic device.

Additionally, the program control method may further include: receiving post-adjustment feedback data from the implantable electronic device via the communication device; and transmitting the post-adjustment feedback data to the terminal device via the network for enquiry by the user.

Additionally, the program control method may further include, subsequent to the reception of the post-adjustment feedback data from the implantable electronic device via the communication device, storing the post-adjustment feedback data.

Additionally, in the program control method, the enquiry request may contain identity information of the user, wherein the program control method further includes, subsequent to the reception of the enquiry request from the terminal device via the network and prior to the transmission of the processed feedback data to the terminal device, determining, based on the identity information of the user in the enquiry request, whether the user is authentic; and if the user is authentic, proceeding to the step of transmitting the processed feedback data to the terminal device.

Additionally, in the program control method, the feedback data may contain an identifier of the implantable electronic device, wherein the program control method further includes, concurrently with the storage of the processed feedback data, correlating the identifier of the implantable electronic device to the processed feedback data so that a correlation between the identifier of the implantable electronic device and the processed feedback data is established, wherein the enquiry request further contains the identifier of the implantable electronic device, and wherein the step of transmitting the processed feedback data to the terminal device includes: obtaining the processed feedback data correlated to the implantable electronic device based on the established correlation; and transmitting the processed feedback data correlated to the implantable electronic device to the terminal device.

BRIEF DESCRIPTION OF THE DRAWINGS

Exemplary description of one or more embodiments will be given below with reference to the corresponding accompanying drawings, but the embodiments are not limited to this description. Like reference numerals indicate similar or identical elements throughout the drawings, which are not necessarily drawn to scale, unless otherwise stated.

DETAILED DESCRIPTION OF PREFERRED EMBODIMENTS

In order that the objectives, subject matter and advantages of embodiments of the present invention may be more clearly understood, a number of embodiments of the invention will now be described with reference to the accompanying drawings. However, those of ordinary skill in the art will appreciate that although numerous technical details are set forth in the following description to provide reader with a better understanding of the present application, the subject matter sought to be protected in this application can be achieved without these technical details or based on various changes or modifications made to the embodiments disclosed hereinafter.

Figure 1:
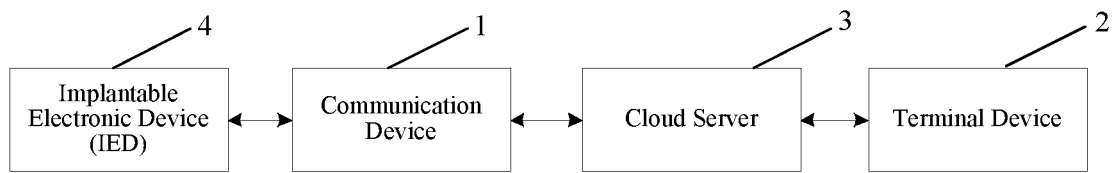
FIG. 1 is a schematic block diagram of a programming system for an implantable electronic device according to a first embodiment of the present invention.

A first embodiment of the present invention relates to a programming system for an implantable electronic device, which, as shown in FIG. 1, includes at least one communication device 1 and a server 3. It is to be noted that the number of communication device(s) 1 shown in FIG. 1 is only exemplary and illustrative. In practice, the programming system may include one server 3 and multiple communication devices 1, and the multiple communication devices 1 are distributed in different locations (as required by the practical applications). The server 3 may be, in particular, a cloud server 3.

In another embodiment of the present invention, the program control system may further include one or more terminal devices 2. When there are multiple terminal devices 2, the multiple terminal devices 2 may also be distributed in different locations.

In particular, the communication device 1 is configured to acquire feedback data from at least one implantable electronic device 4 (as a non-limiting example, one is shown) and upload the feedback data to the cloud server 3. The implantable electronic device 4 is abbreviated and referred to hereinafter as the "IED" 4. The communication device 1 may be a small electronic device, and each patient may be provided with such a communication device 1 so that he/she may immediately upload feedback data upon receiving an enquiry request. The communication device 1 may be, for example, a mobile phone. In this way, patients are allowed to use electronic devices that they usually use to upload feedback data. In order to facilitate the communication device 1 to acquire the feedback data from the IED 4 that is deployed in the body of a patient, the communication device 1 may communicate in the same way as the IED 4. For example, when the IED 4 is a cardiac pacemaker communicating by radio frequency (RF), the communication device 1 may also communicate by RF and communicate with the IED 4 by RF, and the feedback data acquired by the communication device 1 may be pacing data of the patient. Additionally, the communication device 1 may be connected to the cloud server 3 via a wireless or wired network so that it can upload the feedback data to the cloud server 3.

In this embodiment, since hardware cost of the communication device 1 is not high, when hardware upgrading for the communication device 1 is necessary, it may be overall replaced, without posing a great cost burden.

The cloud server 3 is configured to process, for example, to perform a search, parameter configuration or another operation on, the feedback data and store the processed feedback data. Dedicated software for analyzing and managing the feedback data may be installed on the cloud server 3 (e.g., the same as installed on the conventional programmers). The continuous advancement of medical technology requires repeated upgrading of the dedicated software for more scientific analysis and management of the feedback data. In this embodiment, a technician of the manufacturer may directly upgrade the cloud server 3 via the network, without needing to visit individual hospitals that are using their products and field upgrade software on the programmers. This makes upgrading an easier task.

The terminal device 2 is configured to retrieve the processed feedback data from the cloud server for enquiry by a user. The terminal device 2 may be a mobile phone, a tablet computer, laptop computer or the like. An application is installed on the terminal device 2 and is capable of retrieving and displaying the processed feedback data to the user. The user may be a physician, the manufacturer's technician, or even the patient. The application on the terminal device 2 may retrieve the feedback data automatically or in response to a trigger initiated by the user. After checking and analyzing the processed feedback data on the terminal device 2, if the manufacturer's technician or the physician determines a need to adjust parameters of the IED 4, he/she may transmit adjustment commands to the cloud server 3.

The terminal device 2 may maintain a history of processed feedback data, which can contribute to better analysis by the physician or manufacturer's technician.

The terminal device 2 is installed with the application capable of retrieving and displaying the processed feedback data to the user. When replacing the terminal device 2 with a new one, the user can only need to reinstall the application, without incurring any additional cost. Upon a need to upgrade the application itself, the new version of the application may be transmitted to the user via the network and installed later by the user. This task is easy to perform.

Compared to the existing programmers implemented as monolithic physical structures, the system of this embodiment is a distributed architecture where the patient can transmit feedback data to the cloud server 3 via the wireless network, with the user being able to get access to the feedback data from the IED 4 in the patient on the cloud server 3 via the wireless network.

Therefore, compared to the conventional programmers, the embodiments of the present invention entail a program control system distributed in terms of functions and components. That is, the program control system is composed of physically separate components including the communication device, the terminal device and the cloud server. In this way, the various components in the program control system can be hardware upgraded separately. That is, hardware of each of the communication device, the terminal device and the cloud server can be independently upgraded. Therefore, the program control system of this application is reduced in hardware upgrading cost (compared to the existing programmers, which must be overall replaced for hardware upgrading). Moreover, software upgrading of each component in the program control system is allowed to be achieved in a timely and individual way (any component can be immediately upgraded upon a new software version becoming available) so that the latest advancements in the medical science and technology can be applied to the various components in the program control system to result in more scientific analysis and management of feedback data. These make upgrading an easy task. Further, the program control system entails a processing mode for use on a cloud platform, in which the communication device acquires feedback data from the IED deployed in the patient's body and uploads the acquired feedback data to the cloud server for processing. The manufacturer's technician and the physician can retrieve the processed feedback data from the cloud server onto their terminal devices and know conditions of the patient from the data. This provides operational convenience to the patient, the physician and the technician who may be in different locations. Furthermore, storing the processed feedback data on the cloud server can prevent loss of such data and enable consistent analysis over a long history.

Figure 2:
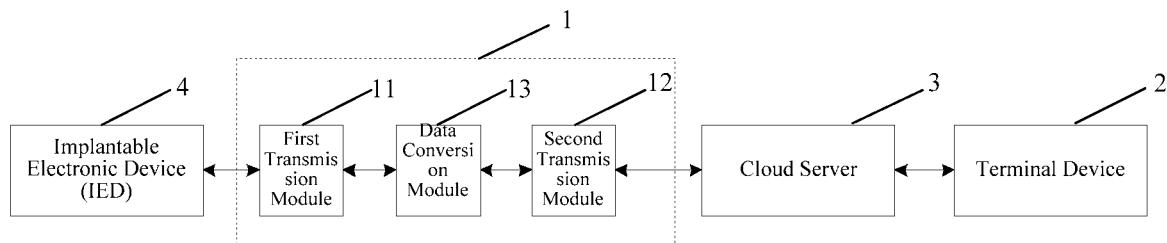
FIG. 2 is a schematic block diagram of a programming system for an implantable electronic device according to a second embodiment of the present invention.

A second embodiment of the present invention relates to a program control system for an implantable electronic device. The second embodiment is a refined implementation of the first embodiment. The refinement lies essentially in that, as shown in FIG. 2, the communication device 1 according to this embodiment includes a first transmission module 11, a second transmission module 12 and a data conversion module 13.

In this embodiment, the data conversion module 13 is connected to both the first transmission module 11 and the second transmission module 12.

The first transmission module 11 is configured to acquire feedback data in a first format from the IED 4. The feedback data in the first format may be analog feedback data. The first transmission module 11 may include at least one of a short-range wireless communication module (e.g., Bluetooth, NFC, RF, etc.), a long-range RF identification module and a network cable interface. The first transmission module 11 may communicate in the same way as the IED 4 so that it can easily acquire analog feedback data from the IED 4.

The data conversion module 13 may include an analog-to-digital converter and a digital-to-analog converter. The analog-to-digital converter may be configured to convert the feedback data in the first format acquired by the first transmission module 11 from the IED 4 into feedback data in a second format. The feedback data in the second format may be digital feedback data.

It is to be noted that, while the feedback data in the first format has been described as analog feedback data, and the feedback data in the second format as digital feedback data, above in this embodiment, the embodiment is not limited thereto, because any data format that complies with the communication rules is considered to fall within the scope of this application.

The second transmission module 12 is configured to upload the feedback data in the second (digital) format to the cloud server 3. The second transmission module 12 may include a wireless network module enabling the module to be communicatively connected to the cloud server 3 wirelessly, for example, by WiFi, 4G, 3G, etc. Additionally, the second transmission module 12 may include a network cable interface enabling the module to be communicatively connected to the cloud server 3 via a wired network. However, this embodiment is not limited thereto, as the second transmission module 12 may include both the wireless network module and the network cable interface so that one of them may be appropriately selected as practically required.

When the manufacturer's technician or the physician determines that it is necessary to adjust parameters of the IED 4 based on an analysis on the processed feedback data displayed on the terminal device 2, he/she may transmit adjustment commands in the second (digital) format to the cloud server 3, the cloud server 3 may then pass them on to the communication device 1. Upon receipt of the adjustment commands by the second transmission module 12 in the communication device 1, the digital-to-analog converter therein may convert the adjustment commands from the second (digital) format into the first (analog) format, and the first transmission module 11 may then send the adjustment commands in the first (analog) format to the IED 4 to allow the corresponding adjustments of the IED 4.

Compared to the first embodiment, this embodiment provides a particular structure of the communication device as well as particular communication methods of the first and second transmission modules.

Figure 3:
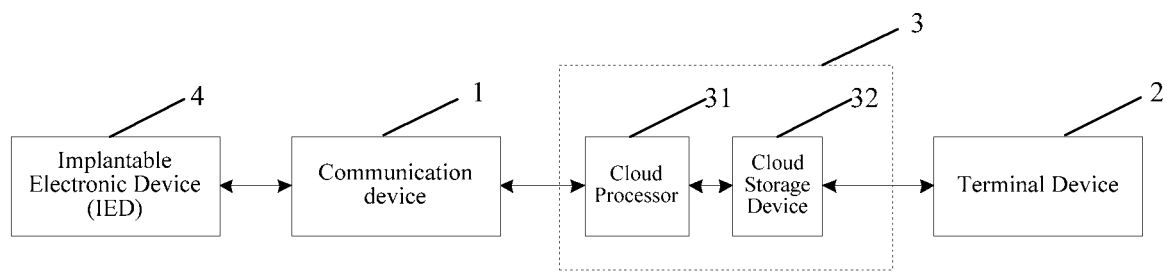
FIG. 3 is a schematic block diagram of a programming system for an implantable electronic device according to a third embodiment of the present invention.

A third embodiment of the present invention relates to a program control system for an implantable electronic device. The third embodiment is a refined implementation of the first embodiment. The refinement lies essentially in that, as shown in FIG. 3, the cloud server 3 according to this embodiment includes a cloud processor 31 and a cloud storage device 32.

The cloud processor 31 is configured to process the feedback data (e.g., the feedback data in the digital format in the second embodiment) and store the processed feedback data on the cloud storage device 32.

Preferably, the IED 4 in the patient's body may have an identifier associated with a document created to store feedback data in the form directly acquired from the IED 4 and the processed feedback data. In other words, for each patient, a document for storing his/her history data may be created for subsequent enquiry and analysis.

Compared to the first embodiment, this embodiment provides a particular structure of the cloud server. It is to be noted that this embodiment may also be considered as a refined implementation of the second embodiment, with the same beneficial effects being still achieved.

Figure 4:
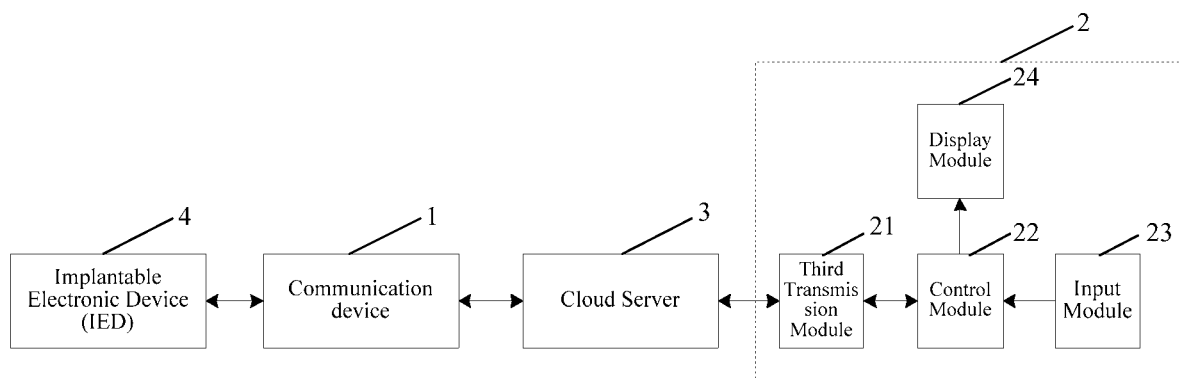
FIG. 4 is a schematic block diagram of a programming system for an implantable electronic device according to a fourth embodiment of the present invention.

A fourth embodiment of the present invention relates to a program control system for an implantable electronic device. The fourth embodiment is a refined implementation of the first embodiment. The refinement lies essentially in that, as shown in FIG. 4, the terminal device 2 according to this embodiment includes a third transmission module 21, a control module 22, an input module 23 and a display module 24.

In this embodiment, the control module 22 is connected to all of the third transmission module 21, the input module 23 and the display module 24.

The control module 22 is configured to acquire the processed feedback data from the cloud server 3 via the third transmission module 21 and cause the display module 24 to display the processed feedback data. The terminal device 2 may be a mobile phone, a tablet computer, a laptop computer or the like and may acquire the processed feedback data from the cloud server 3 via a wired network, or a wireless network (e.g., WiFi, 4G; 3G; etc.).

The input module 23 is configured to input the adjustment commands for the IED 4.

The control module 22 is also configured to transmit the adjustment commands to the cloud server 3 via the third transmission module 21.

The cloud server 3 is also configured to, upon receipt of the adjustment commands, generate adjustment data for the IED 4, and send the adjustment data to the IED 4 via the communication device 1 to allow the corresponding adjustments of the IED 4. After the adjustments have been effected in the IED 4, the communication device 1 is configured to receive post-adjustment feedback data from the IED 4 and transmit such post-adjustment feedback data to the cloud server 3.

Upon receipt of the post-adjustment feedback data from the IED 4 via the communication device 1, the cloud server 3 is configured to send the post-adjustment feedback data to the terminal device 2 for enquiry by the user.

According to this embodiment, when the manufacturer's technician or the physician determines that it is necessary to adjust parameters of the IED 4 based on an analysis on the processed feedback data displayed on the terminal device 2 by the display module 24 thereof, he/she may generate adjustment commands and send the adjustment commands to the cloud server 3 via the third transmission module 21 in the terminal device 2. Upon receipt of the adjustment commands for the IED 4, the cloud server 3 (e.g., the cloud processor 31 in the cloud server 3) may generate adjustment data for the IED 4 based on the adjustment commands and send the generated adjustment data to the communication device 1, the communication device 1 (e.g., the first transmission module 11 therein) may then transmit the adjustment data further to the IED 4 so that the corresponding parameter adjustments can be effected in the IED 4. After this, the communication device 1 may receive post-adjustment feedback data from the IED 4 and send the post-adjustment feedback data to the cloud server 3, the cloud server 3 may then transmit the post-adjustment feedback data further to the terminal device 2 for enquiry by the user (i.e., the manufacturer's technician, the physician, or even the patient).

Compared to the first embodiment, this embodiment provides a particular structure of the terminal device. It is to be noted that this embodiment may also be considered as a refined implementation of the second or third embodiment, with the same beneficial effects being still achieved.

It is to be noted that the various modules in this embodiment are all logical modules. In practical applications, any of the logical modules may be implemented by a physical module or part thereof, or by a combination of multiple physical modules. In addition, in order to emphasize the inventiveness of the present invention, modules not closely related to the problem sought to be solved by the invention are not mentioned in this embodiment. However, this does not imply that such modules are precluded from this embodiment.

A fifth embodiment of the present invention relates to a program control method for an implantable electronic device, for use on a cloud server including a cloud processor and a cloud storage device.

Figure 5:
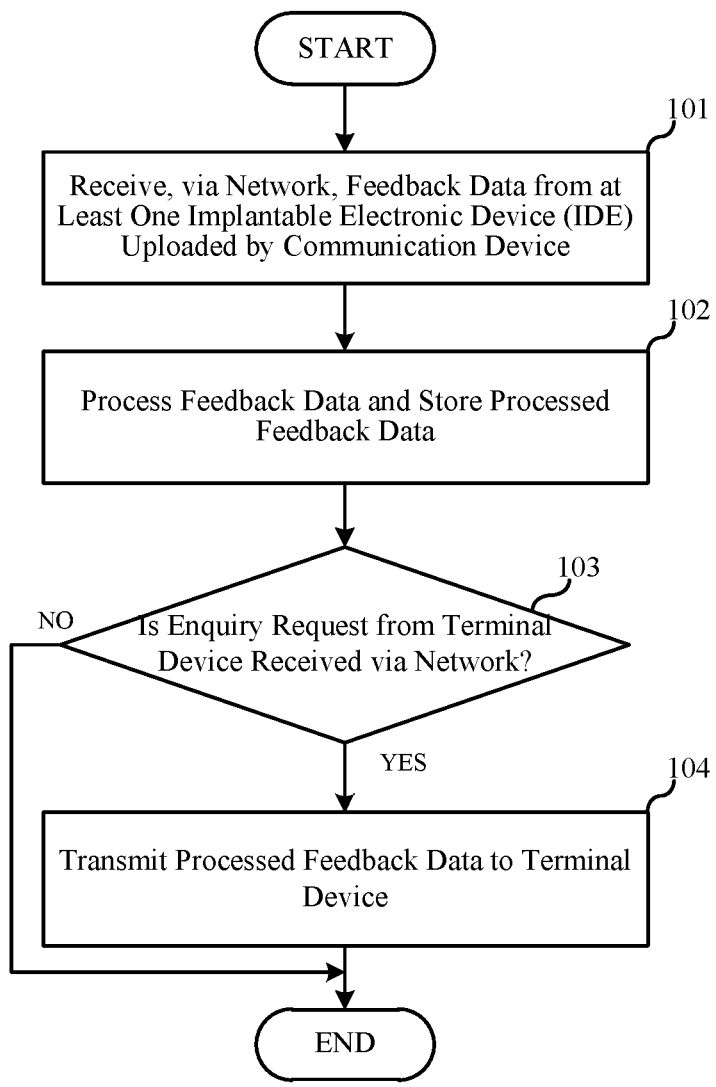
FIG. 5 is a detailed flowchart of a programming method for an implantable electronic device according to a fifth embodiment of the present invention.

FIG. 5 is a flowchart of the program control method for an implantable electronic device according to this embodiment.

In step 101, feedback data from at least one implantable electronic device (IED) uploaded by a communication device is received via a network.

Specifically, the communication device 1 in a program control system for an implantable electronic device as schematically illustrated in FIG. 1 acquires the feedback data from the at least one IED 4 and uploads the feedback data to the cloud server 3. The cloud server 3 receives, via a wired or wireless network, the feedback data from the at least one IED 4 uploaded by the communication device 1.

In step 102, the feedback data is processed and the processed feedback data is stored.

Specifically, the cloud processor 31 in the cloud server 3 (see FIG. 3) processes the feedback data and stores the processed feedback data on the cloud storage device 32. As such, the processed feedback data can be retrieved by a user.

The program control method may further include step 103, in which it is determined whether an enquiry request is received from a terminal device via the network. If the determination is positive, the control method proceeds to step 104. Otherwise, the control method ends.

Specifically, when the manufacturer's technician, the physician or even the patient himself/herself desires to view the processed feedback data from the IED 4 in the patient's body, he/she may transmit an enquiry request via the terminal device 2. When the cloud server 3 detects that the enquiry request has been received from the terminal device via the network, the control method proceeds to step 104. Otherwise, the control method ends.

In step 104, the processed feedback data is transmitted to the terminal device. Specifically, the processed feedback data sent from the cloud server 3 may be displayed on the terminal device 2 for enquiry by the user who may be the physician, the manufacturer's technician or even the patient. When the manufacturer's technician or the physician determines, based on an analysis on the processed feedback data displayed on the terminal device 2, that parameter adjustments are necessary for the IED 4, he/she may transmit adjustment commands to the cloud server 3.

This embodiment corresponds to the foregoing first to fourth embodiments and can be implemented in combination therewith. All the technical details described above in connection with the first to fourth embodiments are equally applicable to this embodiment, and all the benefits of the first to fourth embodiments can be equally achieved in this embodiment. Therefore, a repeated description thereof will be omitted. Similarly, all the technical details described in connection with this embodiment are equally applicable to the foregoing first to fourth embodiments.

Compared to the conventional programmers, the embodiments of the present invention entail a program control system distributed in terms of functions and components. That is, the program control system is composed of physically separate components including the communication device and the cloud server. In this way, the various components in the program control system can be hardware upgraded separately. That is, hardware of each of the communication device, the terminal device and the cloud server can be independently upgraded. Therefore, the program control system of this application is reduced in hardware upgrading cost (compared to the existing programmers, which must be overall replaced for hardware upgrading). Moreover, software upgrading of each component in the program control system is allowed to be achieved in a timely and individual way (any component can be immediately upgraded upon a new software version becoming available) so that the latest advancements in the medical science and technology can be applied to the various components in the program control system to result in more scientific analysis and management of feedback data. These make upgrading an easy task. Further, the program control system entails a processing mode for use on a cloud platform, in which the communication device acquires feedback data from the IED deployed in the patient's body and uploads the acquired feedback data to the cloud server for processing. The manufacturer's technician and the physician can retrieve the processed feedback data from the cloud server onto their terminal devices and know conditions of the patient from the data. This provides operational convenience to the patient, the physician and the technician who may be in different locations. Furthermore, storing the processed feedback data on the cloud server can prevent loss of such data and enable consistent analysis over a long history.

A sixth embodiment of the present invention relates to a program control method for an implantable electronic device. This embodiment is a modified implementation of the fifth embodiment, and the modification lies essentially in that this embodiment provides a particular approach for effecting adjustments in the IED 4.

Figure 6:
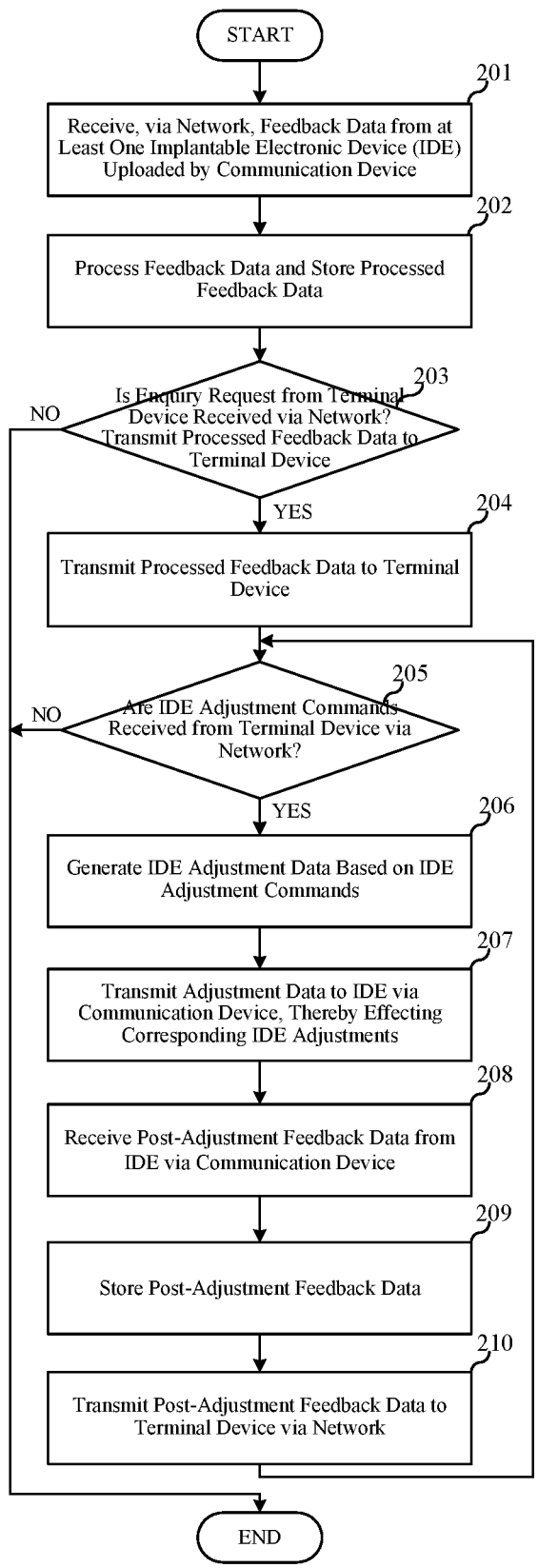
FIG. 6 is a detailed flowchart of a programming method for an implantable electronic device according to a sixth embodiment of the present invention.

A flowchart of the program control method for an implantable electronic device according to this embodiment is shown in FIG. 6.

Steps 201 to 204 in this method are substantially identical to steps 101 to 104 and will not be described in any further detail, and steps 205 to 210 additionally included in this method will now be described.

In step 205, it is determined whether adjustment commands for the IED have been received from the terminal device via the network. If the determination is positive, the control method proceeds to step 206. Otherwise, the control method ends.

Specifically, after the processed feedback data is sent to the terminal device in step 204 (corresponding to step 104 in the fifth embodiment), the manufacturer's technician or the physician may view the processed feedback data displayed on the terminal device 2. When determining that parameter adjustments are necessary for the IED 4 based on an analysis on the processed feedback data, he/she may transmit adjustment commands to the cloud server 3. Upon the cloud server 3 receiving the adjustment commands for the IED 4 from the terminal device via the network, the control method proceeds to step 206. Otherwise, it can be known that the manufacturer's technician or the physician does think it is necessary to adjust parameters of the IED 4 in the patient's body, and the method ends accordingly.

In step 206, adjustment data for the IED is generated based on the adjustment commands for the IED.

Specifically, the cloud processor 31 in the cloud server 3 may generate the adjustment data for the IED 4 based on the received adjustment commands for the IED 4.

In step 207, the adjustment data is transmitted to the IED by the communication device so that corresponding adjustments can be effected in the IED.

Specifically, the cloud server 3 may send the adjustment data to the communication device 1, and the first transmission module 11 in the communication device 1 may then pass the adjustment data on to the IED 4. As such, corresponding adjustments can be effected in the IED 4. That is, corresponding parameters of the IED 4 are adjusted.

The program control method may further include step 208, in which post-adjustment feedback data from the IED is received via the communication device.

Specifically, after the corresponding adjustments are effected in the IED 4, the communication device 1 may receive post-adjustment feedback data from the IED 4 and transmit such post-adjustment feedback data to the cloud server 3.

In step 209, the post-adjustment feedback data is stored.

Specifically, preferably, the cloud server 3 may store the post-adjustment feedback data received from the communication device 1 as a historical record so that the user (i.e., the manufacturer's technician, the physician, or even the patient) can view the post-adjustment feedback data at any time as desired.

The program control method may further include step 210, in which the post-adjustment feedback data is transmitted to the terminal device via the network. Steps 209 and 210 can be sequentially performed in the order as described in this embodiment. That is, step 210 follows step 209. However, in other embodiments of this application, step 209 may follow step 210, or the steps 209 and 210 may be performed in parallel.

Specifically, the cloud server 3 may send the post-adjustment feedback data to the terminal device 2 for enquiry by the user.

In this embodiment, all or some of steps 205 to 210 may form a loop, in which if the user finds, from data displayed on the terminal device 2, that the adjustments made to the IED 4 are ineffective and fail to render the adjusted IED 4 operable with the adjusted parameters, he/she may produce new adjustment commands for the IED 4 to cause all or some of steps 205 to 210 to be performed for another time. This cyclic process may be repeated until the user determines, from data displayed on the terminal device 2, that effective adjustments to the IED 4 have been attained and the adjusted IED 4 is operating with the adjusted parameters.

Compared to the fifth embodiment, this embodiment provides a particular approach for adjusting the implantable electronic device (IED) and thus maintaining or improving reliability thereof.

A seventh embodiment of the present invention relates to a program control method for an implantable electronic device. This embodiment is a modified implementation of the fifth embodiment, and the modification lies essentially in that, in this embodiment, the enquiry request contains user identity information, with which the identity of the user who sent the enquiry request can be authenticated.

Figure 7:
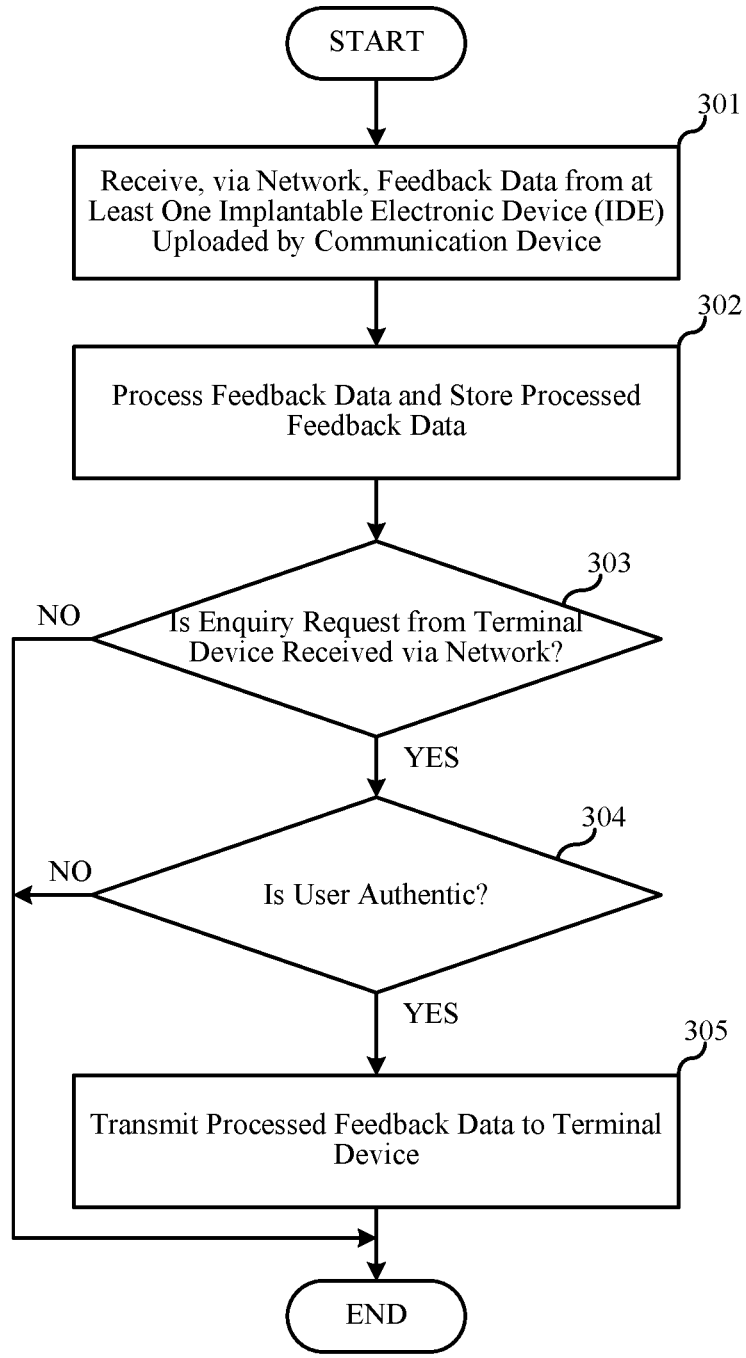
FIG. 7 is a detailed flowchart of a programming method for an implantable electronic device according to a seventh embodiment of the present invention.

A flowchart of the program control method for an implantable electronic device according to this embodiment is shown in FIG. 7.

Steps 301 to 303 in this method are substantially identical to steps 101 to 103, and step 305 to step 104. These steps will not be described in any further detail, and step 304 additionally included in this method will now be described.

In step 304, it is determined whether the user is authentic. If it is, then the control method proceeds to step 305. Otherwise, the control method ends.

Specifically, the cloud server 3 may maintain identity information of multiple users. Therefore, it can be determined whether the user is authentic, based on the identity information contained in the received enquiry request. If the identity information in the enquiry request has pre-existed in the cloud server 3, control proceeds to step 305 in which the processed feedback data is transmitted to the terminal device. Otherwise, it is determined that the user is not authentic, and the method ends. The authentic user may be the manufacturer's technician, the physician, or even the patient.

Compared to the fifth embodiment, the user's identity information is authenticated in this embodiment, and the processed feedback data is accessible to the user only when he/she is an authorized user. It is to be noted that this embodiment may also be considered as a refined implementation of the sixth embodiment, with the same beneficial effects being still achieved.

An eighth embodiment of the present invention relates to a program control method for an implantable electronic device. This embodiment is a modified implementation of the seventh embodiment, and the modification lies essentially in that, in this embodiment, an identifier of the IED 4 is correlated to the processed feedback data.

Figure 8:
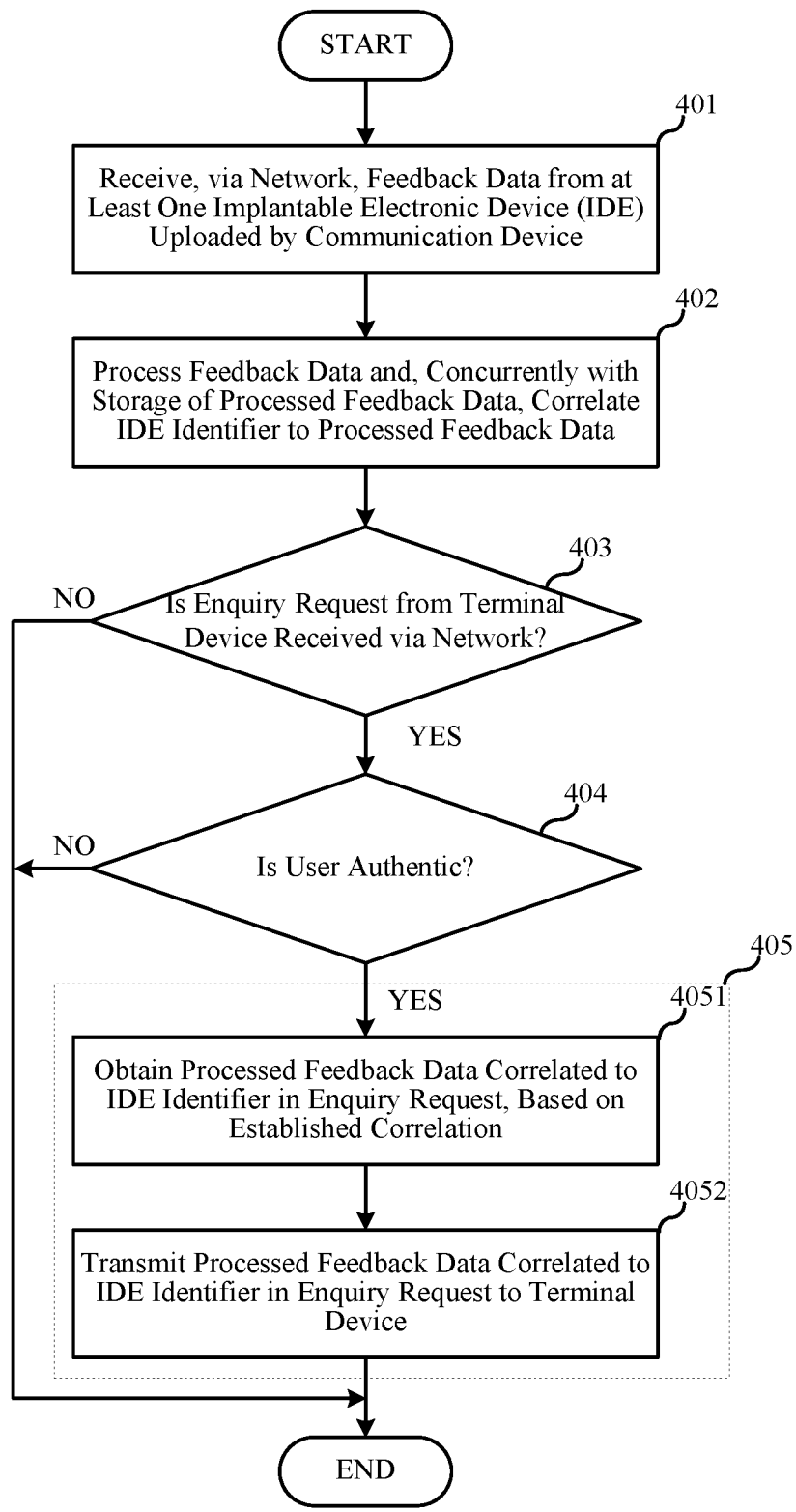
FIG. 8 is a detailed flowchart of a programming method for an implantable electronic device according to an eighth embodiment of the present invention.

A flowchart of the program control method for an implantable electronic device according to this embodiment is shown in FIG. 8.

Step 401 in this method is substantially identical to step 301, and steps 403 and 404 are substantially identical to steps 303 and 304. These steps will not be described in any further detail. Major differences between the method of this embodiment and that of the seventh embodiment will now be described.

In step 402, the feedback data is processed, and concurrently with the storage of the processed feedback data, an identifier of the IED is correlated with the processed feedback data.

Specifically, the cloud server 3 may process the feedback data and store the processed feedback data. At the same time, it may correlate the identifier of the IED 4 to the processed feedback data, i.e., establishing a correlation between the identifier of the IED 4 and the processed feedback data. Since each IED 4 has an identifier corresponding to a patient, this will also establish correlation between the patient and the processed feedback data.

In step 405, the processed feedback data is transmitted to the terminal device. This step may in particular include the following sub-steps.

In 4051, based on the established correlation, the processed feedback data from the IED whose identifier is contained in the enquiry request is obtained.

Specifically, the cloud server 3 may maintain historical feedback data from multiple patients' IEDs 4, and the enquiry request may further contain the identifier of the IED 4 in the concerned patient. Based on the correlation established between the identifier of the IED 4 and the processed feedback data, the cloud server 3 may obtain the processed feedback data correlated to the identifier of the IED 4 contained in the enquiry request. That is, it may obtain the processed feedback data for the patient in question.

In 4052, the processed feedback data correlated to the identifier of the IED in the enquiry request is transmitted to the terminal device.

Specifically, the cloud server 3 may send the processed feedback data correlated to the identifier of the IED 4 in the enquiry request to the terminal device 2, which is then displayed thereon for enquiry of the user.

Compared to the seventh embodiment, the identifier of the IED is correlated to the processed feedback data in accordance with this embodiment. This facilitates the acquisition of the processed feedback data correlated to the IED specified in the enquiry request. That is, acquition of the processed feedback data for a specified patient is made possible. It is to be noted that this embodiment may also be considered as a refined implementation of the sixth or seventh embodiment, with the same beneficial effects being still achieved.

Those of ordinary skill in the art will appreciate that the foregoing embodiment are particular embodiments presented to enable practicing of the present invention. In practical applications, various changes can be made to their form and details without departing from the spirit and scope of the invention.

What is claimed is:

1. A program control method for an implantable electronic device, for use on a cloud server, the program control method comprising:

receiving, via a network, feedback data from at least one implantable electronic device uploaded by a communication device;

processing the feedback data and storing the processed feedback data, upon receipt of an enquiry request from a terminal device of the user via the network, transmitting the processed feedback data to the terminal device for enquiry by the user, determining whether an adjustment command for the implantable electronic device has been received from the terminal device of the user via the network;

if the adjustment command has been received, generating adjustment data for the implantable electronic device based on the adjustment command; and transmitting the adjustment data to the implantable electronic device via the communication device, thereby achieving corresponding adjustment of the implantable electronic device, receiving post-adjustment feedback data from the implantable electronic device via the communication device; and transmitting the post-adjustment feedback data to the terminal device via the network for enquiry by the user, wherein the processed feedback data is available for retrieval by a user, wherein hardware of each of the communication device, the terminal device and the cloud server is independently upgraded.

2. The program control method for an implantable electronic device of claim 1, further comprising, subsequent to the reception of the post-adjustment feedback data from the implantable electronic device via the communication device, storing the post-adjustment feedback data.

3. The program control method for an implantable electronic device of claim 1, wherein the enquiry request contains identity information of the user, and wherein the program control method further comprises, subsequent to the reception of the enquiry request from the terminal device via the network and prior to the transmission of the processed feedback data to the terminal device:

determining, based on the identity information of the user contained in the enquiry request, whether the user is authentic; and if the user is authentic, proceeding to the step of transmitting the processed feedback data to the terminal device.

4. The program control method for an implantable electronic device of claim 1, wherein the feedback data contains an identifier of the implantable electronic device, wherein the program control method further comprises:

concurrently with the storage of the processed feedback data, correlating the identifier of the implantable electronic device to the processed feedback data so that a correlation between the identifier of the implantable electronic device and the processed feedback data is established, wherein the enquiry request further contains the identifier of the implantable electronic device, and wherein the step of transmitting the processed feedback data to the terminal device comprises:

obtaining the processed feedback data correlated to the implantable electronic device based on the established correlation; and transmitting the processed feedback data correlated to the implantable electronic device to the terminal device.

5. The program control method for an implantable electronic device of claim 1, wherein the communication device is directly connected to the implantable electronic device, so that the communication device is able to directly acquire the feedback data from the implantable electronic device.

6. The program control method for an implantable electronic device of claim 1, wherein the cloud server has a program control software installed thereon, wherein the cloud server is configured to process the feedback data based on the program control software, and wherein the program control software on the cloud server is updated directly via a network.

7. The program control method for an implantable electronic device of claim 1, wherein the feedback data contains an identifier of the implantable electronic device, the terminal device is configured to transmit an enquiry request further containing the identifier of the implantable electronic device, based on a correlation established between the identifier of the implantable electronic device and the processed feedback data, the cloud server is further configured to obtain the processed feedback data correlated to the identifier of the implantable electronic device.

8. The program control method for an implantable electronic device of claim 1, wherein the communication device is only configured to provide the following data transmission: transmit the feedback data from the implantable electronic device to the cloud server, and transmit the adjustment data generated by the cloud server to the implantable electronic device.

\* \* \* \* \*